United States Patent
Shiozaki et al.

(10) Patent No.: US 11,305,101 B2
(45) Date of Patent: Apr. 19, 2022

(54) APPLICATOR FOR MEDICAL-USE LIQUIDS

(71) Applicant: OTSUKA PHARMACEUTICAL FACTORY, INC., Tokushima (JP)

(72) Inventors: Mari Shiozaki, Tokushima (JP); Kazumasa Hashimoto, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 361 days.

(21) Appl. No.: 15/580,872

(22) PCT Filed: Jun. 17, 2016

(86) PCT No.: PCT/JP2016/002924
§ 371 (c)(1),
(2) Date: Dec. 8, 2017

(87) PCT Pub. No.: WO2016/208166
PCT Pub. Date: Dec. 29, 2016

(65) Prior Publication Data
US 2018/0161561 A1 Jun. 14, 2018

(30) Foreign Application Priority Data

Jun. 25, 2015 (JP) .................................. 2015-128033
Sep. 2, 2015 (JP) .................................. 2015-172589

(51) Int. Cl.
*A61M 35/00* (2006.01)
*A61K 31/79* (2006.01)
(Continued)

(52) U.S. Cl.
CPC ......... *A61M 35/006* (2013.01); *A61K 31/155* (2013.01); *A61K 31/79* (2013.01); *A61K 33/18* (2013.01)

(58) Field of Classification Search
CPC .......................... A61M 35/003; A61M 35/006
See application file for complete search history.

(56) References Cited

U.S. PATENT DOCUMENTS

| | | |
|---|---|---|
| 5,288,159 A | 2/1994 | Wirt |
| 6,099,184 A | 8/2000 | Koptis |
| | (Continued) | |

FOREIGN PATENT DOCUMENTS

| | | |
|---|---|---|
| CN | 103438753 | 12/2013 |
| JP | 06-277297 | 10/1994 |
| | (Continued) | |

OTHER PUBLICATIONS

Official Communication issued in Patent Application No. PCT/JP2016/002924, dated Sep. 6, 2016, along with an English translation thereof.
(Continued)

*Primary Examiner* — Tatyana Zalukaeva
*Assistant Examiner* — Ilya Y Treyger
(74) *Attorney, Agent, or Firm* — Greenblum & Bernstein, P.L.C.

(57) ABSTRACT

An applicator for medical-use liquids includes a handle having a hollow cylindrical member, a container incorporated in the cylindrical member, and a cleaving member of the container; and an applying section having an attachment plate of an application pad (integrally) fixed to a lower end of the cylindrical member to be an inclined cross section and the application pad fixed to the attachment plate. The attachment plate has a bank section formed thick at a peripheral edge, a base bottom section formed as a recess in a center, an inclined outflow hole opened inclinedly with respect to the base bottom section near the base bottom section center such that the solution flows out toward an attachment plate distal end direction, and a weir provided in an arcuate or crescent shape. A flow of the solution flowed out from the inclined outflow hole is reversed to flow backward by the weir.

17 Claims, 5 Drawing Sheets

(51) Int. Cl.
*A61K 33/18* (2006.01)
*A61F 13/40* (2006.01)
*A61K 31/155* (2006.01)
*A61K 31/15* (2006.01)

(56) References Cited

U.S. PATENT DOCUMENTS

| | | | |
|---|---|---|---|
| 2006/0072962 A1* | 4/2006 | Cybulski | A61M 35/006 401/205 |
| 2010/0168638 A1* | 7/2010 | Korogi | A61M 35/006 604/3 |
| 2014/0186092 A1* | 7/2014 | McDonald | A61M 35/003 401/143 |
| 2014/0234004 A1 | 8/2014 | Thorpe et al. | |
| 2014/0316352 A1 | 10/2014 | Durham et al. | |

FOREIGN PATENT DOCUMENTS

| | | |
|---|---|---|
| JP | 2004-515285 | 5/2004 |
| JP | 2008-515484 | 5/2008 |
| JP | 2009-526624 | 7/2009 |
| JP | 2011-104415 | 6/2011 |
| JP | 2012-513879 | 6/2012 |
| JP | 2012-513880 | 6/2012 |
| JP | 2013-023271 | 2/2013 |
| JP | 2013-023282 | 2/2013 |
| JP | 2015-514551 | 5/2015 |
| WO | 02/046089 | 6/2002 |
| WO | 2006/041801 | 4/2006 |
| WO | 2007/095576 | 8/2007 |
| WO | 2009/076612 | 6/2009 |
| WO | 2010/078361 | 7/2010 |
| WO | 2010/078363 | 7/2010 |
| WO | 2013/162882 | 10/2013 |
| WO | 2013/163552 | 10/2013 |

OTHER PUBLICATIONS

Official Communication issued in Patent Application No. PCT/JP2016/002924, dated Jan. 4, 2018, along with an English language translation thereof.

* cited by examiner

[Figure 1]
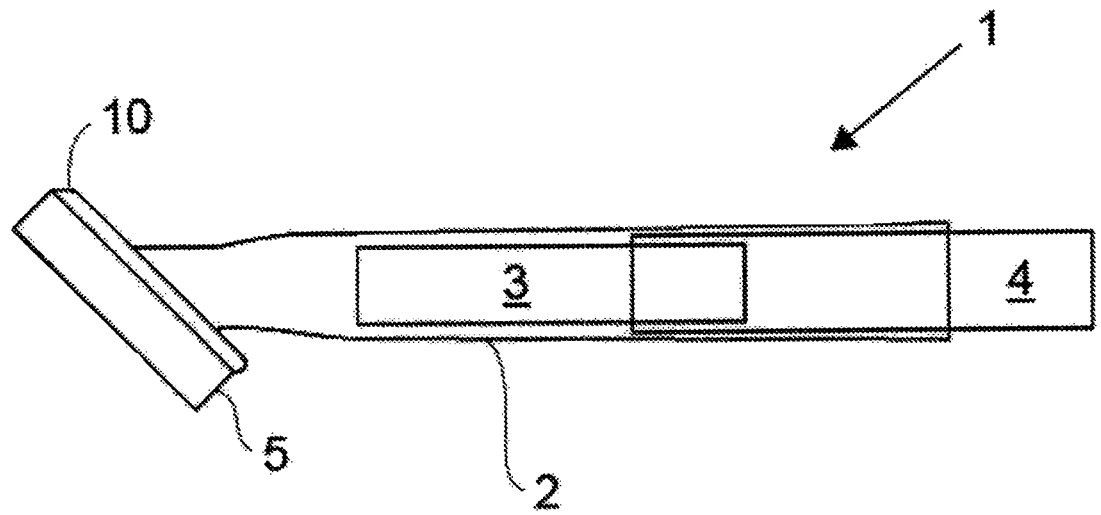
[Figure 2]
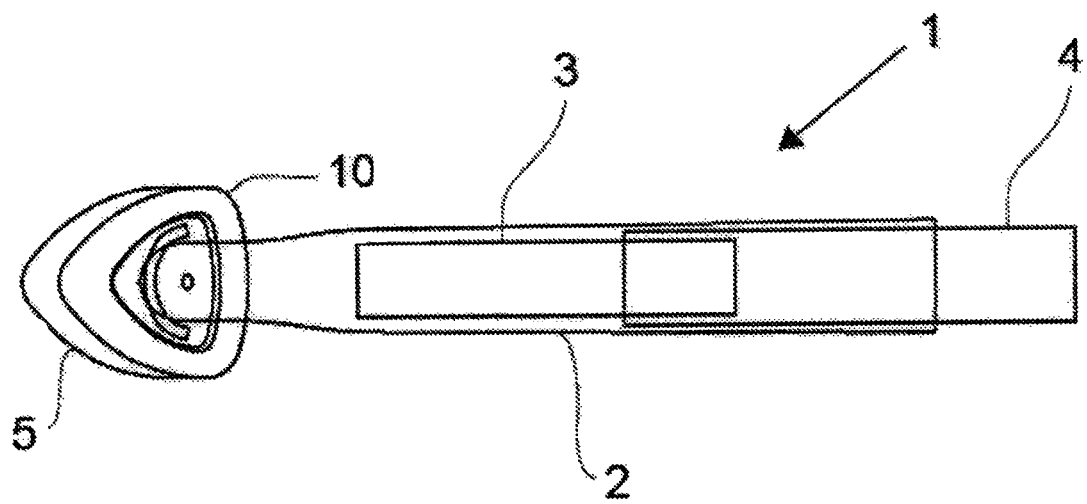

[Figure 3]
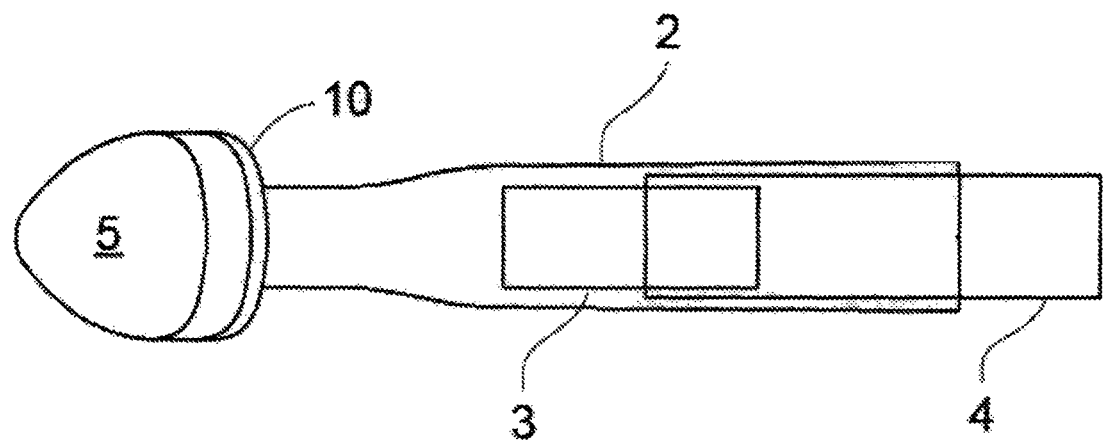
[Figure 4]
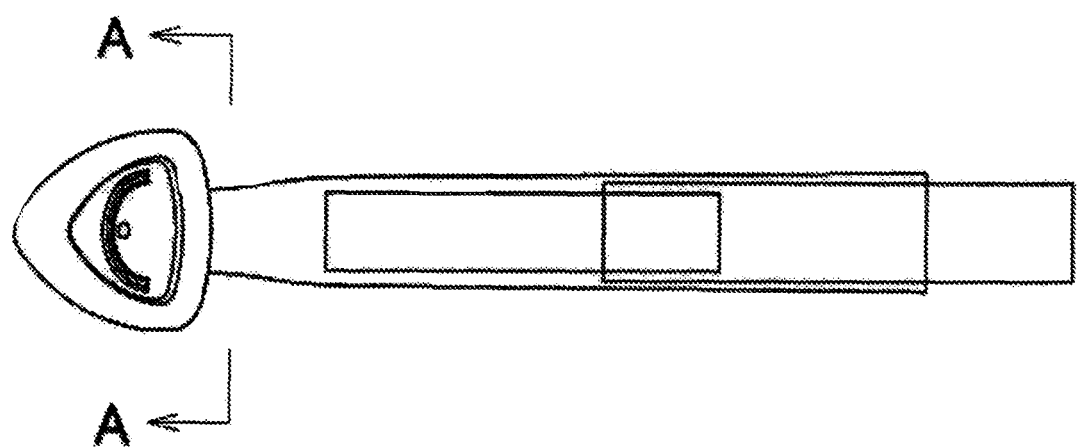

[Figure 5]
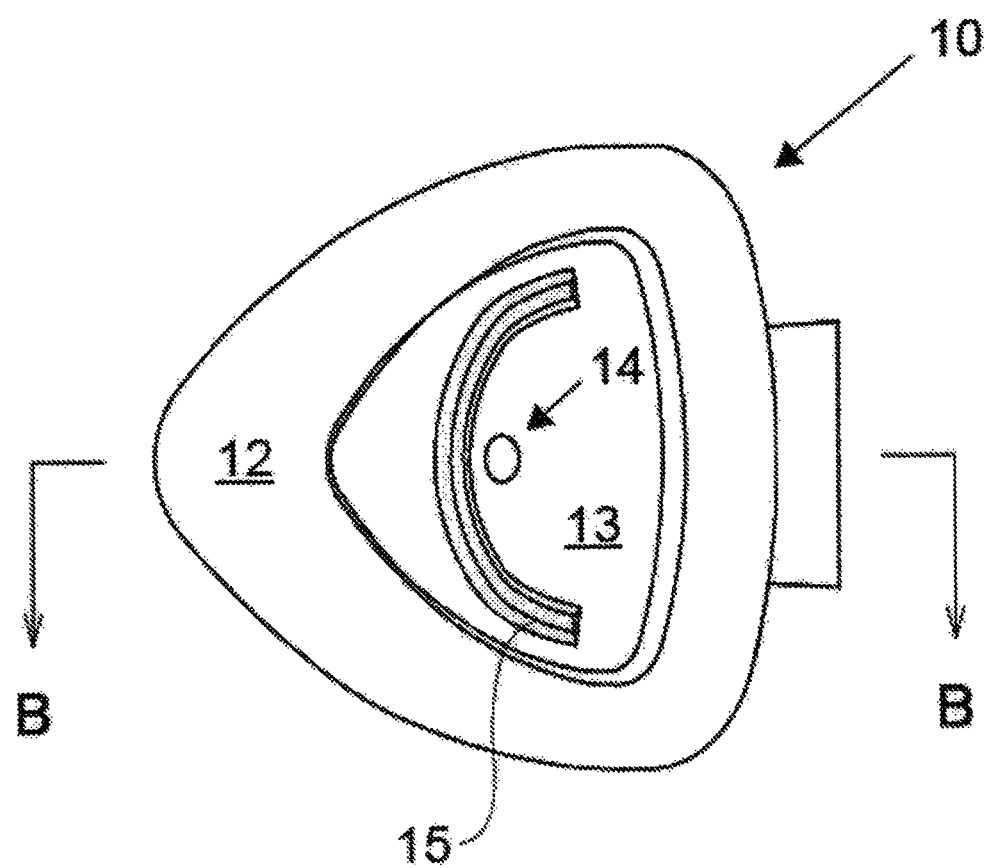

[Figure 6]
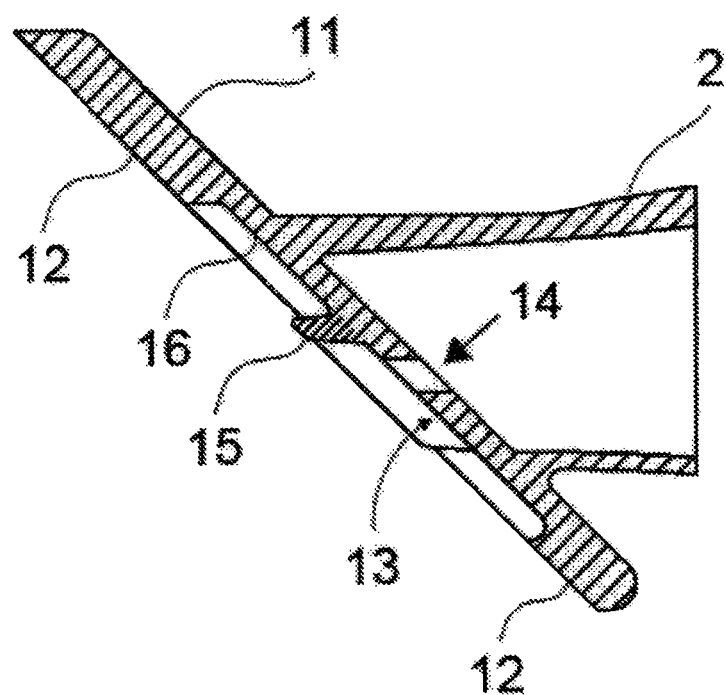

[Figure 7]
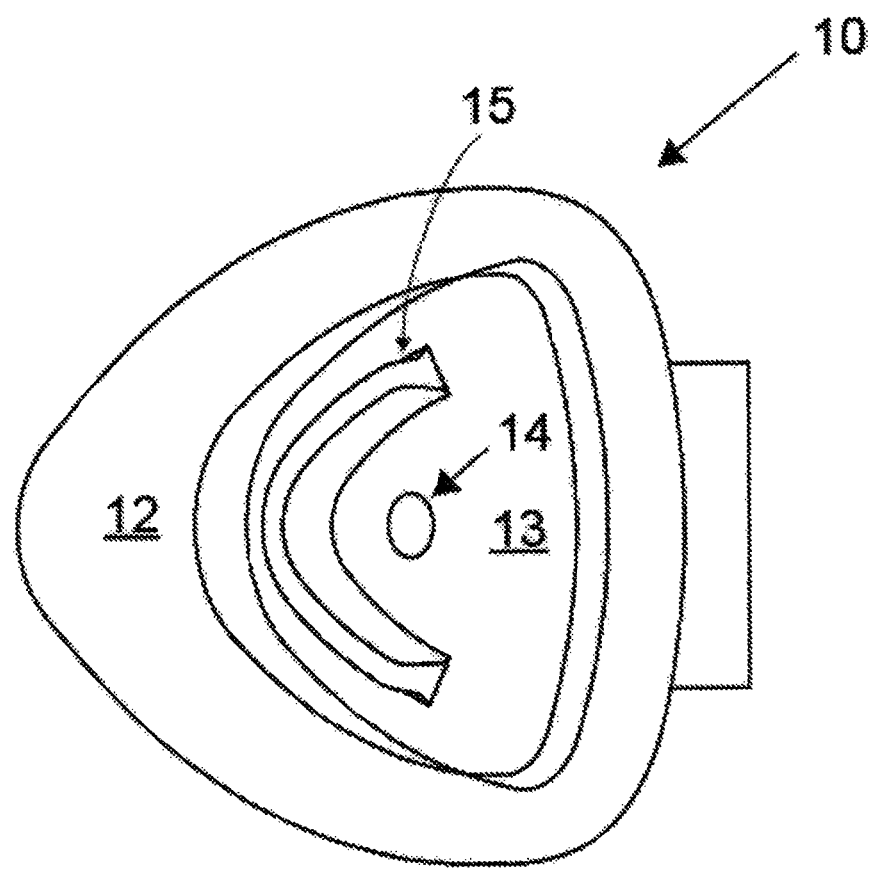

APPLICATOR FOR MEDICAL-USE LIQUIDS

TECHNICAL FIELD

The present invention relates to an applicator for applying medical-use liquids such as disinfection liquid to skin, the applicator being particularly useful in the field of a surgical operation.

BACKGROUND ART

As an applicator for applying a surgical cleaning agent and disinfection liquid before an operation to skin, there have been known a liquid applicator including a feeding device for applying liquid stored in a breakable tank container to a surface, the liquid applicator being particularly useful for applying a surgical cleaning or coating agent before an operation to skin (patent document 1), a portable liquid applicator including a flexible elongated hollow cylinder body that receives a glass ampoule containing liquid and including a breaking mechanism for the ampoule in order to subdivide and discharge the liquid (patent document 2), and an applicator including a hollow elongated member including a container, a flange extending to the outer side in the radial direction from the hollow elongated member, and a distributor element attached to the flange, the applicator being an applicator for applying or supplying liquid, and the distributor element including at least two orifices, a projecting element that separates the at least two orifices, and an absorbing pad attached to the first side of the distributor element (patent document 3).

There have been known an applicator for applying a disinfection agent to a desired surface and for selectively removing undesirable by-products deriving from the disinfection agent (patent document 4), an applicator device including a packet for storing fluid and a handle including a flexible lid configured to apply an external pressure to the packet to compress the packet and make it possible to release the fluid from the packet (patent document 5), an applicator including an elongated hollow body, an application pad, and an actuator sleeve inserted into the hollow body, when the actuator sleeve including a longitudinal-direction projecting section moves in the hollow body, the actuator sleeve acting on a lid section of a liquid container in the hollow body to open the lid section and discharging the liquid from the liquid container to the application pad (patent document 6), and a liquid applicator consisting of an outer container consisting of a main body section formed in a cylindrical shape, a porous body impregnated with a drug solution attached to one end portion of the main body section, and a cap including a slit fit in the other end portion and an inner container sealed by a lid material including a knob section, the drug solution being encapsulated in the inner container, the inner container being housed in the main body section, and the knob section being folded back in the direction of the cap and projecting to the outer side of the outer container through the slit (patent document 7).

There have been known a liquid applicator consisting of a main body extended in a cylindrical shape, the main body including an opening at one end portion, and a porous body having an impregnating ability being attached to the other end portion, a bottle filled with a drug solution, a mouth section of the bottle being sealed by a seal material, and a substantially cylindrical connecting body that couples the main body and the bottle, a screw-like section for screwing with a mouth of the bottle being formed on the inner surface of the connecting body and a convex rib movable in association with the opening being formed on the outer surface of the connecting body, a substantially S-shaped guide groove for guiding the convex rib being formed on a sidewall of the opening and an intermediate shelf being formed on the inner surface of the opening, and an inner cylinder whose distal end is acute having a hole for breaking the seal material being formed on the inner surface of the intermediate shelf in the direction of the mouth section along an axis (patent document 8) and an applicator including a lever formed integrally with a hollow main body suitable for receiving a liquid filling ampoule, the lever including a hinge, a gripping section, and a foot section, the foot section being positioned adjacent to the ampoule and, when the lever is pushed down, breaking the ampoule to discharge liquid (patent document 9).

PRIOR ART DOCUMENTS

Patent Documents

[Patent Document 1] Japanese unexamined Patent Application Publication No. H6-277297

[Patent Document 2] Japanese unexamined Patent Application Publication (Translation of PCT Application) No. 2004-515285

[Patent Document 3] Japanese unexamined Patent Application Publication (Translation of PCT Application) No. 2008-515484

[Patent Document 4] Japanese unexamined Patent Application Publication (Translation of PCT Application) No. 2009-526624

[Patent Document 5] Japanese unexamined Patent Application Publication (Translation of PCT Application) No. 2012-513879

[Patent Document 6] Japanese unexamined Patent Application Publication (Translation of PCT Application) No. 2012-513880

[Patent Document 7] Japanese unexamined Patent Application Publication No. 2013-23271

[Patent Document 8] Japanese unexamined Patent Application Publication No. 2013-23282

[Patent Document 9] Japanese unexamined Patent Application Publication (Translation of PCT Application) No. 2015-514551

SUMMARY OF THE INVENTION

Object to be Solved by the Invention

An object of the present invention is to provide an applicator for medical-use liquids in which an appropriate amount of medical-use liquid such as disinfection liquid uniformly exudes from an application pad, the applicator being able to accurately apply a predetermined amount of medical-use liquid.

Means to Solve the Object

In a type of an applicator in which a container, which stores liquid such as disinfection liquid, is incorporated in a hollow cylindrical member including an application pad at a lower end, and wherein the container is cleaved in order to release and discharge the liquid into the cylindrical member, cause the liquid to flow out from a hole in a bottom section of the cylindrical member, cause the flowed-out liquid to permeate through the application pad, and apply the liquid to skin, there has been a problem in that the liquid suddenly and one-sidedly flows out immediately after the cleavage of the liquid container and non-uniformly permeates into the application pad and, as a result, the liquid drips or leaks from the application pad before the application or during the application, or conversely, an amount of liquid permeated into the application pad partially decreases and the liquid sometimes cannot be smoothly and uniformly applied by the application pad.

Therefore, in order to solve the problem, in a process of variously examining a shape of the application pad, a surface state of the application pad, a material of the application pad, a capacity of a recess surrounded by a peripheral edge bank section in an attachment plate of the application pad, size of an inclined outflow hole opened to incline in a base bottom section of the attachment plate, a method of cleaving the container, a type of a disinfectant, and the like, the inventors have reached an idea that it would be possible to adjust a flow rate and a flowing direction by providing a weir. As a result of repeating trial and error concerning a shape, height, and inclination of the weir, the inventors have found that the problem can be solved by providing an arcuate or crescent weir with the inclined outflow hole being located on the center side of the arc, in particular, providing a weir slightly higher than the peripheral edge bank section in the attachment plate.

That is, the present invention is as described below.

[1] An applicator for medical-use liquids including: a handle section comprising a hollow cylindrical member, a liquid container incorporated in the cylindrical member, and a cleaving means of the liquid container; and an applying section comprising an attachment plate of an application pad fixed to a lower end of the cylindrical member to be an inclined cross section, and the application pad fixed to the attachment plate, wherein, the attachment plate is provided with a bank section formed thick at a peripheral edge, a base bottom section formed as a recess in a center, an inclined outflow hole opened inclinedly with respect to the base bottom section such that a solution released and discharged near the base bottom section center from the liquid container flows out toward an attachment plate distal end direction, and a weir provided in an arcuate shape or a crescent shape in the base bottom section in an attachment plate distal end direction from the inclined outflow hole, the inclined outflow hole being located on a center side of the arc.

[2] The applicator according to [1], wherein the cylindrical member is formed in a cylindrical shape having a taper that narrows downward.

[3] The applicator according to [1] or [2], wherein the cleaving means of the liquid container is an actuator sleeve inserted into the cylindrical member.

[4] The applicator according to any one of [1] to [3], wherein the application pad and the attachment plate are formed in a substantially rice ball shape.

[5] The applicator according to any one of [1] to [4], wherein a center axis of the cylindrical member is inclined at 40 to 50° with respect to an attachment plate upper surface on the basis of the attachment plate upper surface.

[6] The applicator according to any one of [1] to [5], wherein the weir is 0.1 to 1 mm higher than the bank section in a vertical direction with respect to an attachment plate upper surface on the basis of the attachment plate upper surface.

[7] The applicator according to [6], wherein the weir is 0.25 to 0.75 mm higher than the bank section.

[8] The applicator according to any one of [1] to [7], wherein the weir provided in an arcuate shape or a crescent shape is inclined at 40 to 50° in a direction further away from the center side of the arc toward an upper end of the weir on the basis of a base bottom section surface.

Effect of the Invention

With the applicator of the present invention, medical-use liquid such as disinfection liquid does not drip from the application pad, an appropriate amount of medical-use liquid such as the disinfection liquid uniformly exudes from the application pad, and a predetermined amount of medical-use liquid can be accurately applied to skin.

BRIEF DESCRIPTION OF DRAWINGS

[FIG. 1] It is a front view of an applicator (25 mL) of the present invention.

[FIG. 2] It is a plan view of the applicator (25 mL) of the present invention.

[FIG. 3] It is a bottom view of the applicator (25 mL) of the present invention.

[FIG. 4] It is a bottom view of the applicator (25 mL) of the present invention from which an application pad has been removed.

[FIG. 5] It is an enlarged view of an A-A part of FIG. 4 (a front view of an attachment plate of the application pad).

[FIG. 6] It is a sectional view of a B-B part of FIG. 5.

[FIG. 7] It is a front view of an attachment plate of an application pad of an applicator (10 mL) of the present invention in another mode.

MODE OF CARRYING OUT THE INVENTION

In the following explanation, the right side in FIGS. 1 to 4 is referred to as "upward" and the left side in FIGS. 1 to 4 is referred to as "downward". A distal end refers to the left side in FIGS. 5 and 7 and left obliquely upward in FIG. 6.

An applicator for medical-use liquids of the present invention is not particularly limited as long as the applicator includes: a handle section including a hollow cylindrical member, a liquid container incorporated in the cylindrical member, and cleaving means of the liquid container; and an applying section including an attachment plate of an application pad fixed to a lower end of the cylindrical member to be an inclined cross section and the application pad stuck to the attachment plate. However, the applicator has a characteristic in the structure of the attachment plate of the application pad. Concerning the handle section and the application pad, the techniques disclosed in patent documents 1 to 9 described above can be basically applied.

The hollow elongated cylindrical member forming the handle section of the applicator of the present invention only has to have a structure in which the liquid container incorporated in the cylindrical member is cleaved by the cleaving means, liquid is released and discharged from the liquid container, and the released and discharged liquid flows out from an inclined outflow hole provided in a base bottom section of the attachment plate without being lost from an upper part of the cylindrical member. Examples of the cylindrical member include elongated hollow cylindrical members that are circular, elliptical, and rectangular in cross section and have a length of 10 to 20 cm and a diameter or a long side of 2 to 4 cm. However, a tapered cylindrical shape reduced in diameter downward can be suitably illustrated. The attachment plate of the application pad is integrally fixed to the lower end of the cylindrical container to be an inclined cross section. When an attachment plate upper surface is set as a level reference, the center axis of the cylindrical member is erected to be inclined at 30 to 60°, desirably 40 to 50° with respect to the attachment plate upper surface. The cylindrical member is made of plastic and manufactured from olefin-based resin such as polyethylene or polypropylene, polyethylene terephthalate resin, polyamide resin, MBS resin such as methyl methacrylate butadiene-styrene or methyl methacrylate butadiene-styrene n-butyl acrylate, or the like. However, selection of resin and setting of thickness only have to be performed as appropriate according to moldability, rigidity, and the like. Examples of a molding method include injection molding and extrusion molding.

The liquid container only has to be a container in which medical-use liquid such as disinfection liquid or cleaning liquid is stored, which can be incorporated in the cylindrical member, from which the liquid is released and discharged by the cleaving means, and which can cause the released and discharged liquid to flow out from the inclined outflow hole provided in the base bottom section of the attachment plate without being lost from the upper part of the cylindrical member. Examples of the liquid container include a brittle ampoule, a collapsible container, a perforable container, and a container with a removable cap.

The cleaving means only has to be means that can cleave the liquid container incorporated in the cylindrical member, release and discharge the liquid from the liquid container, and cause the released and discharged liquid to flow out from the inclined outflow hole provided in the base bottom section of the attachment plate without being lost from the upper part of the cylindrical member. Examples of the cleaving means include ampoule breaking means such as a lever for a brittle ampoule incorporated in the cylindrical member having a cap at the upper end (patent documents 1 to 4 and 9), external pressure applying means for compressing a bucket that stores liquid (patent document 5), an actuator sleeve that detaches a lid of the liquid container by pushing the actuator sleeve downward in the cylindrical member (patent document 6), and seal peeling means for unsealing the liquid container (patent documents 7 and 8). However, the actuator sleeve for detaching the lid of the liquid container can be suitably illustrated.

Examples of the shape of the application pad include a substantially rice ball shape (omusubi-shape), a rectangular shape, an oval shape, a circular shape, a triangular shape, and an elliptical shape in a plan view having thickness of approximately 1.5 to 2 mm. However, the application pad is desirably formed in a substantially rice ball shape in terms of smoothness and handleability. As the material of the application pad, a porous material having a characteristic of causing liquid such as disinfection liquid to permeate and impregnate can be suitably illustrated. However, other woven fabric and nonwoven fabric can also be used. Examples of the material of such a porous material and the like include resin such as polyolefin-based resin, polyurethane-based resin, and polyethylene terephthalate-based resin and cellulose-based fiber. Such an application pad can be attached to the top surface of a bank section formed in the attachment plate by heat seal or an adhesive.

The attachment plate is provided with a bank section formed thick at a peripheral edge and formed flat on a top surface, a base bottom section formed as a recess in a center and formed flat on a bottom surface, an inclined outflow hole opened inclinedly with respect to the base bottom section such that the solution flows out near the base bottom section center and toward an attachment plate distal end direction, and a weir provided in an arcuate shape or a crescent shape in the base bottom section in the attachment plate distal end direction from the inclined outflow hole, the inclined outflow hole being located on a center side of the arc. The shape of the attachment plate is desirably the same shape as the application pad. For example, in the case of the substantially rice ball shape, the shape of the base bottom section is also the substantially rice ball shape. The inclined outflow hole is provided near the center portion of the base bottom section.

The inclined outflow hole is opened in an oval shape that is long in the front-rear direction on a base bottom section surface. As the size of the hole, usually, a long diameter is approximately 4 to 6.5 mm and a short diameter is approximately 3 to 5 mm depending on the size of the applicator. The weir is provided in the base bottom section in the arcuate shape or the crescent shape with the inclined outflow hole being located on the center side of the arc. However, the position of the inclined outflow hole with respect to the weir can be determined as appropriate from a position on a chord of the arc to a position closer to the arc between the arc and the chord according to the size of the base bottom section. A shortest distance from the inclined outflow hole (oval) distal end to the weir is desirably set to 2 to 3 mm.

The weir provided in the arcuate shape or the crescent shape is desirably inclined at 40 to 50° in a direction concentrically away from the center side of the arc toward the upper end of the weir on the basis of the base bottom section surface. Since the weir is formed as an inclined curved surface with respect to the base bottom section surface, it is possible to efficiently reverse a flow of liquid blocked by the weir to flow backward. As a result, it is possible to restrict a one-sided flow of the solution to the distal end direction and cause the solution to uniformly permeate into the application pad.

The weir is desirably set higher than the bank section in the vertical direction with respect to the attachment plate upper surface on the basis of the attachment plate upper surface. A high portion (hereinafter sometimes referred to as "projecting section" as well) is desirably, for example, 0.1 to 1 mm, in particular, 0.25 to 0.75 mm. Since the weir is higher than the bank section, the top section of the weir bites into the application pad. Consequently, it is possible to prevent a liquid flow from climbing over the weir and surely reverse the liquid flow to flow backward. In particular, when the weir has an inclined curved surface shape, the liquid flow easily climbs over the weir. Therefore, it is desirable to set the weir higher than the bank section, cause the top section of the weir to bite into the application pad, and surely reverse the liquid flow to flow backward.

Examples of the medical-use liquid include disinfection liquid and cleaning liquid. More specifically, examples of the medical-use liquid include povidone-iodine liquid, ethanol liquid, isopropanol liquid, potassium iodide liquid, benzalkonium chloride liquid, benzethonium chloride liquid, chlorhexidine gluconate liquid, glutaraldehyde liquid, and olanexidine [1-(3,4-dichlorobenzyl)-5-octylbiguanide] liquid. Two or more kinds of these liquids can be mixed and used. Such medical-use liquids can be applied to a local region and used immediately before an operation.

The medical-use liquid is not particularly limited as long as the medical-use liquid is liquid obtained by converting an effective component such as a disinfection component or a cleaning component into a liquid agent. The medical-use liquid may be an aqueous formulation obtained by diluting the effective component with purified water or may be an alcohol formulation obtained by diluting the effective component with purified alcohol such as ethanol or isopropanol or a water solution of the purified alcohol. The concentration of the effective component is optional. Alcohol concentration in the case of the alcohol formulation is also optional. In the medical-use liquid, besides the effective component, additives usually used as the aqueous formulation and the alcohol formulation, for example, an antiseptic agent, a moisturizing agent, a thickening agent, a non-ionic surface active agent, a cationic surface active agent, an antioxidant, an aromatic, and a coloring agent can also be used. The viscosity of the liquid agent is not limited as long as the viscosity is in a range not practically causing a hindrance in applying the liquid agent using the application pad. However, the viscosity is desirably 0.5 to 15.0 mPa·s. The applicator of the present invention can also be suitably used for a low-viscosity liquid agent that easily leaks, that is, a liquid agent having viscosity of 0.5 to 4.0 mPa·s, in particular, 0.5 to 2.5 mPa·s. The viscosity is a numerical value measured according to a viscosity measuring method for liquids and a viscosity measuring method by a cone-plate type rotation viscometer of JIS Z8803. A measurement temperature is 20° C.

The applicator of the present invention is applied to a local region of a target immediately before an operation. First, the liquid container is broken using the cleaving means of the handle section and the liquid is released and discharged into the cylindrical member from the liquid container by seal removal, lid removal, or the like and caused to flow out from the inclined outflow hole to the applying section. Most of the liquid flowed out from the inclined outflow hole flows in the attachment plate distal end direction. However, the liquid is blocked by the weir to once reverse and flow backward and take a roundabout route from left and right two gaps between the bank section and the weir to flow in the base bottom section distal end direction. The flow of the liquid is adjusted. After the liquid sufficiently permeates into the application pad, the liquid is applied to skin.

An implementation form of the applicator for medical-use liquids of the present invention is explained below with reference to the drawings. An applicator 1 shown in FIGS. 1 to 6 is configured from a handle section including a hollow cylindrical member 2, a liquid container 3 incorporated in the cylindrical member 2, and an actuator sleeve 4 inserted into the cylindrical member 2, and an applying section including an attachment plate 10 of an application pad 5 fixed to the lower end of the cylindrical member 2 to be an inclined cross section and the application pad 5 having a substantially rice ball shape stuck to the attachment plate 10. The cylindrical member 2 and the attachment plate 10 are made of methyl methacrylate butadiene-styrene resin and integrally molded. The application pad 5 is made of polyethylene and has a percentage of voids of 87%.

The cylinder-shaped cylindrical member 2 having a taper narrowing downward has a length (the center axis) of approximately 18.5 cm and a maximum outer diameter of approximately 28 mm. The center axis of cylindrical member 2 is inclined at approximately 45° with respect to an attachment plate upper surface 11 on the basis of the attachment plate upper surface 11. The attachment plate is also formed in a substantially rice ball shape, which is a similar shape slightly smaller than the application pad 5. The attachment plate 10 has a length of approximately 6 cm in the front-rear direction and a width of approximately 4.5 cm in a rear part.

The attachment plate 10 is provided with a bank section 12 formed thick at a peripheral edge, a base bottom section 13 formed as a recess in a center, an inclined outflow hole 14 opened inclinedly with respect to the base bottom section 13 such that the solution flows out near the base bottom section center and toward an attachment plate distal end direction, and a weir 15 provided in an arcuate shape in the base bottom section 13 in an attachment plate distal end direction from the inclined outflow hole 14, the inclined outflow hole 14 being located on a center side of the arc. The depth of the base bottom section 13 with respect to the bank section 12 is approximately 2 mm. The diameter (an intermediate value of a long diameter and a short diameter) of the inclined outflow hole 14 is approximately 3.5 mm (25 mL) or approximately 4.5 mm (10 mL). The inclined outflow hole 14 is provided closer to an arc between the arc and a chord.

The weir 15 is 0.5 mm higher than the bank section 12 in the vertical direction with respect to the attachment plate upper surface 11 (a projecting section of 0.5 mm) on the basis of the attachment plate upper surface 11. The weir 15 provided in the arcuate shape is provided to incline at 45° in a direction concentrically away from the center side of the arc toward the upper end of the weir 15 on the basis of a base bottom section surface 16. The thickness of the weir 15 is approximately 1.5 mm.

EXAMPLE 1

A liquid leak test of olanexidine liquid (OPB) was carried out using the applicator (25 mL) of the present invention including the application pad made of polyethylene having the percentage of voids of 87% and the weir including the projecting section. The hole diameter (the intermediate value of the long diameter and the short diameter) of the inclined outflow hole was set to 3.25 mm, 3.5 mm, or 4.0 mm. The projecting section was set to 0.25 mm, 0.5 mm, or 0.75 mm. A result is shown in Table 1. In the table, a denominator of a fraction notation represents the total number of samples and a numerator represents the number of liquid leaking samples. As it is seen from Table 1, there was no liquid leak when the hole diameter of the inclined outflow hole was 3.25 to 4.0 mm.

TABLE 1

| Number of OPB liquid leak specimens | Projecting section 0.25 mm | Projecting section 0.5 mm | Projecting section 0.75 mm |
|---|---|---|---|
| Hole diameter 3.25 mm | | 0/26 | |
| Hole diameter 3.5 mm | 0/24 | 0/26 | 0/23 |
| Hole diameter 4.0 mm | | 0/23 | |

EXAMPLE 2

Liquid leak tests of olanexidine liquid (OPB) and povidone-iodine liquid (PVI) were carried out using the applicator (10 mL) of the present invention including the application pad made of polyethylene having the percentage of voids of 87% and the weir including the projecting section. The hole diameter (the intermediate value of the long diameter and the short diameter) of the inclined outflow hole was set to 4.25 mm or 4.5 mm which was slightly larger than the hole diameter in the example 1. The projecting section was set to 0.25 mm or 0.5 mm. A result is shown in Table 2 and Table 3. As a result, it is seen that a liquid leak hardly occurs even if the hole diameter is increased.

TABLE 2

| Number of OPB liquid leak specimens | Projecting section 0.25 mm | Projecting section 0.5 mm |
|---|---|---|
| Hole diameter 4.25 mm | | 0/23 |
| Hole diameter 4.5 mm | 0/15 | 0/26 |

TABLE 3

| Number of PVI liquid leak specimens | Projecting section 0.25 mm | Projecting section 0.5 mm |
|---|---|---|
| Hole diameter 4.25 mm | | 1/25 |
| Hole diameter 4.5 mm | 2/12 | 0/26 |

COMPARATIVE EXAMPLE

Liquid leak tests of olanexidine liquid (OPB) and povidone-iodine liquid (PVI) were respectively carried out using a conventional applicator (10 mL) and a conventional applicator (25 mL) including an application pad made of polyethylene having a percentage of voids of 87% and not including a weir, and in which hole diameter (the intermediate value of the long diameter and the short diameter) of the inclined outflow hole was set to 2.5 mm. Concerning the PVI, a liquid leak was not found in both of the applicator (10 mL) and the applicator (25 mL). Concerning the OPB, regardless of the hole diameter of 2.5 mm, a considerable liquid leak was found in both of the applicator (10 mL) and the applicator (25 mL).

The olanexidine liquid used in the examples 1 and 2 and the comparative example was a water solution including gluconic acid and polyalkylene glycol in which the concentration of olanexidine was 1.5%. The viscosity of the olanexidine liquid was 1.2 mPa·s. The povidone-iodine liquid used in the example 2 and the comparative example was a 10% povidone-iodine formulation and was a water solution including glycerin, potassium iodide, lauromacrogol, phosphoric anhydride-hydrogen sodium, citric acid hydrate, and sodium hydroxide. The viscosity of the povidone-iodine liquid was 4.5 mPa·s. The viscosity was measured at temperature of 20° C. according to a viscosity measuring method for liquids and a viscosity measuring method by a cone-plate type rotation viscometer of JIS Z8803.

INDUSTRIAL APPLICABILITY

The applicator for medical-use liquids of the present invention is useful in the medical field such as a surgical operation.

EXPLANATION OF LETTERS AND NUMERALS

1 applicator
2 cylindrical member
3 liquid container
4 actuator sleeve
5 application pad
10 attachment plate
11 attachment plate upper surface
12 bank section
13 base bottom section
14 inclined outflow hole
15 weir
16 base bottom section surface

The invention claimed is:

1. An applicator for medical-use liquids that does not cause liquid leakage comprising:
a handle section comprising a hollow cylindrical member, a liquid container incorporated in the cylindrical member, and a cleaver of the liquid container; and
an applying section comprising an attachment plate of an application pad directly fixed to a lower end of the cylindrical member to be an inclined cross section, and the application pad fixed to the attachment plate, wherein
the attachment plate is provided with a bank section which is formed thicker at a peripheral edge, a base bottom section formed as a recess in a center, only one inclined outflow hole penetrating the attachment plate, and opened inclinedly with respect to the base bottom section such that a solution released and discharged near the base bottom section center from the liquid container flows out toward an attachment plate distal end direction, and a weir provided in an arcuate shape or a crescent shape in the base bottom section in the attachment plate distal end direction from the inclined outflow hole, the inclined outflow hole being located on a center side of the arc, wherein the weir is independent and not linked with the bank section, and the weir being 0.1 to 1 mm higher than the bank section in a vertical direction with respect to an attachment plate upper surface on a basis of the attachment plate upper surface.

2. The applicator according to claim 1, wherein the cylindrical member is formed in a cylindrical shape having a taper that narrows downward.

3. The applicator according to claim 1, wherein the cleaver of the liquid container is an actuator sleeve inserted into the cylindrical member.

4. The applicator according to claim 1, wherein a center axis of the cylindrical member is inclined at 40 to 50° with respect to the attachment plate upper surface on a basis of the attachment plate upper surface.

5. The applicator according to claim 1, wherein the weir is 0.25 to 0.75 mm higher than the bank section.

6. The applicator according to claim 1, wherein the weir provided in an arcuate or a crescent shape is inclined at 40 to 50° in a direction further away from a center side of an arc toward an upper end of the weir on a basis of a base bottom section surface.

7. The applicator according to claim 1, wherein the weir is higher than the bank section in the vertical direction with respect to the attachment plate upper surface on a basis of the attachment plate upper surface, and a top section of the weir bites into the application pad.

8. The applicator according to claim 1, wherein the medical-use liquid is a liquid selected from povidone-iodine liquid, ethanol liquid, isopropanol liquid, potassium iodide liquid, benzalkonium chloride liquid, benzethonium chloride liquid, chlorhexidine gluconate liquid, glutaraldehyde liquid, and olanexidine [1-(3,4-dichlorobenzyl)-5-octylbiguanide] liquid, or a mixed liquid of two or more kinds of these.

9. The applicator according to claim 1, wherein the viscosity of the medical-use liquid is 0.5 to 15.0 mPa·s.

10. The applicator according to claim 2, wherein the cleaver of the liquid container is an actuator sleeve inserted into the cylindrical member.

11. The applicator according to claim 10, wherein the application pad and the attachment plate are formed in a substantially rice ball shape.

12. The applicator according to claim 11, wherein a center axis of the cylindrical member is inclined at 40 to 50° with respect to the attachment plate upper surface on a basis of the attachment plate upper surface.

13. The applicator according to claim 12, wherein the weir provided in an arcuate or a crescent shape is inclined at 40 to 50° in a direction further away from a center side of an arc toward an upper end of the weir on a basis of a base bottom section surface.

14. The applicator according to claim 13, wherein the weir is higher than the bank section in a vertical direction with respect to the attachment plate upper surface on a basis of the attachment plate upper surface, and a top section of the weir bites into the application pad.

15. The applicator according to claim 14, wherein the medical-use liquid is a liquid selected from povidone-iodine liquid, ethanol liquid, isopropanol liquid, potassium iodide liquid, benzalkonium chloride liquid, benzethonium chloride liquid, chlorhexidine gluconate liquid, glutaraldehyde liquid, and olanexidine [1-(3,4-dichlorobenzyl)-5-octyl-biguanide] liquid, or a mixed liquid of two or more kinds of these.

16. The applicator according to claim 15, wherein the viscosity of the medical-use liquid is 0.5 to 15.0 mPa·s.

17. The applicator according to claim 2, wherein the weir provided in an arcuate or a crescent shape is inclined at 40 to 50° in a direction further away from a center side of an arc toward an upper end of the weir on a basis of a base bottom section surface.

* * * * *